United States Patent [19]

Ozawa et al.

[11] Patent Number: 6,143,949
[45] Date of Patent: Nov. 7, 2000

[54] METHOD FOR TRANSFERRING GENE

[75] Inventors: Kenjirou Ozawa; Yasunobu Ohkawa, both of Ibaraki; Teruo Ishige, Tokyo, all of Japan

[73] Assignee: Japan as represented by Director General of Ministry of Agriculture, Forestry and Fisheries National Institue of Agrobiological Resources, Ibaraki, Japan

[21] Appl. No.: 09/194,330

[22] PCT Filed: Sep. 26, 1997

[86] PCT No.: PCT/JP97/03445

§ 371 Date: Nov. 24, 1998

§ 102(e) Date: Nov. 24, 1998

[87] PCT Pub. No.: WO98/42857

PCT Pub. Date: Oct. 1, 1998

[30] Foreign Application Priority Data

Mar. 26, 1997 [JP] Japan ..................................... 9/93202

[51] Int. Cl.[7] .............................. A01H 1/00; A01H 4/00; C12N 15/82; C12N 15/87
[52] U.S. Cl. ...................... 800/278; 800/320.2; 800/320; 435/468; 435/474; 435/421
[58] Field of Search ..................................... 800/278, 320, 800/320.2; 435/468, 474, 421

[56] References Cited

FOREIGN PATENT DOCUMENTS 410262666A 10/1998 Japan ............................ C12N 15/09

OTHER PUBLICATIONS

Japanese Journal of Breeding, vol. 46, separate vol. 2 (1996) Kenjiro Ozawa et al. "The efficiency of introduction of giant DNA (100 kb) in the transformation of Oryza sativa by the PEG process". p. 132.
Ashworth et al., "Assembly of High–Resolution Bacterial Artificial Chromosome, P1–Derived Artificial Chromosome, and Cosmid Contigs", Analytical Biochemistry 224:564–571, 1995.
Ausubel et al., "Minipreps of Plasmid DNA", Current Protocols in Molecular Biology 1:1.6.1–2.10.16, 1991.
Datta et al., "Genetically Engineered Fertile Indica–Rice Recovered From Protoplasts", Bio/Technology 8:736–740, 1990.
Duncan et al., "The Production of Callus Capable of Plant Regeneration from Immature Embryos of Numerous Zea Mays Genotypes", Planta 165:322–4332, 1985.
Hamilton et al., "Stable Transfer of Intact High Molecular Weight DNA Into Plant Chromosomes", Proc. Natl. Acad. Sci. USA 93:9975–9979, 1996.
Fujimura et al., "Regeneration of Rice Plants from Protoplasts", Plant Tissue Culture Letters 2(2):74–75, 1985.
Lorz et al., "Advances in Tissue Culture and Progress Towards Genetic Transformation of Cereals", Plant Breeding 100:1–25, 1988.
Ozawa et al., "High–frequency Somatic Embryogenesis from Small Suspension–Cultured Clusters of Cells of an Intersfecific Hybrid of Oryza", Plant Cell, Tissue and Organ Culture 46:157–159, 1996.
Rao et al., "Physical, Chemical and Physiological Parameters for Electroporation–Mediated Gene Delivery Into Rice Protoplasts", Transgenic Research 4:361–368, 1995.
Tada et al., "Efficient Gene Introduction into Rice by Electroporation and Analysis of Transgenic Plants: Use of Electroporation Buffer Lacking Chloride Ions", Theor Appl Genet 80:475–480, 1990.
Tsukahara et al., "Characterization of Factors Affecting Plantlet Regeneration from Rice (Oryza sativa L.) Callus", Bot. Mag. Tokyo 105:227–233, 1992.
Van Eck et al., "Stable Transformation of Tomato Cell Cultures After Bombardment with Plasmid and YAC DNA", Plant Cell Reports 14:299–304, 1995.

*Primary Examiner*—David T. Fox
*Assistant Examiner*—Anne Marie Grünberg
*Attorney, Agent, or Firm*—Fish & Richardson P.C.

[57] ABSTRACT

A method for transferring a long-chain DNA into protoplasts, comprising the steps of: (a) mixing a suspension of protoplasts, polyethylene glycol, and a long-chain DNA to give a final concentration of the DNA of at least 50 μg/ml; (b) collecting, washing, and culturing the protoplasts in a medium; and (c) selecting transformed cells, is provided. By this gene transfer method, long-chain DNA can be conveniently transferred into a wide variety of plant cells.

12 Claims, 3 Drawing Sheets

METHOD FOR TRANSFERRING GENE

TECHNICAL FIELD

The present invention relates to the field of gene engineering, more particularly to a method for transferring genes into plant cells.

BACKGROUND ART

Methods for transferring foreign genes into host cells, that is, the transformation technique, are fundamental techniques in the field of gene engineering. Such methods are used to analyze functions of transferred genes, produce recombinant proteins, gene therapy, generate useful recombinant plants, etc.

Previously developed techniques for transforming plant cells include the electroporation method, the Agrobacterium-mediated method, the microprojectile bombardment method, and the polyethylene glycol method. In the electroporation method, a DNA is transferred using an electric pulse. The Agrobacterium-mediated method utilizes infection by a terrestrial bacterium, Agrobacterium, which causes a plant tumor. In the microprojectile bombardment method, microparticles adsorbing a DNA are shot into cells. The polyethylene glycol method comprises binding a DNA to polyethylene glycol that is a fusion agent and transferring the binding product into cells by (presumably) an endocytosis-like process.

However, these methods cannot introduce macromolecular DNA fragments larger than 25 kb into cells (Carol, M. et al., Proc. Natl. Acad. Sci. U.S.A. 93, 9975 (1996)). For example, it was difficult to apply the above-described transformation methods to isolate and clone genes of a map-base using a gene map made utilizing a restriction fragment length polymorphis (RFLP) marker. In order to transfer a long-chain DNA into cells, attempts were made to improve the above-described transformation methods. Recently, a long-chain DNA was successfully transferred into plant cells by the Agrobacterium-mediated method and the microprojectile bombardment method [Carol, M. et al., Proc. Natl. Acad. Sci. U.S.A. 93, 9975–9979, (1996), Joyce, M. et al., Plant Cell Reports 14, 299–304 (1995)].

However, the Agrobacterium-mediated method has problems in that a foreign gene to be transferred is inserted into a limited vector system and this method cannot be applied to some plant species. The microprojectile bombardment method has disadvantages in that the apparatus used is expensive and the transfer efficiency is low.

In contrast, the polyethylene glycol method is highly applicable since this method can be performed simply if using a purified DNA and can be applied to an unlimited variety of plant cells. However, the transfer of a long-chain DNA into cells by this method has never been reported.

SUMMARY OF THE INVENTION

An objective of the present invention is to provide a convenient method for transferring a gene that enables introducing a long-chain DNA into plant cells and applies to a wide variety of plants.

As a result of intensive investigation to achieve the above-described objective, the present inventors have found that a long-chain DNA can be transferred into plant cells by elevating the concentration of the DNA to be reacted with polyethylene glycol, thereby completing the present invention.

The present invention relates to the polyethylene glycol method of transferring a gene into plant cells. More particularly, it relates to (1) a method for transferring a long-chain DNA into protoplasts, comprising the steps of: (a) mixing a suspension of protoplasts, polyethylene glycol, and a long-chain DNA to give a final concentration of the DNA of at least 50 μg/ml; (b) collecting, washing, and culturing the protoplasts in a medium; and (c) selecting transformed cells, (2) a method for transferring a long-chain DNA into protoplasts, comprising the steps of: (a) mixing a suspension of protoplasts, polyethylene glycol, and a long-chain DNA to give a final concentration of the DNA of at least 100 μg/ml; (b) collecting, washing, and culturing the protoplasts in a medium; and (c) selecting transformed cells, (3) the method of (1) or (2), wherein, in the washing of the protoplast in the step of collecting, washing, and culturing the protoplasts in a medium, a precipitated DNA is dissolved by allowing it to stand or by gently stirring to suspend the protoplasts, (4) the method of any one of (1) to (3), wherein said long-chain DNA is of 100 kb or more, (5) the method of any one of the above-described (1) to (3), wherein said protoplasts are derived from a monocotyledonous plant, (6) the method of (5), wherein said monocotyledonous plant is a plant of the genus Gramineae, and (7) the method of (6), wherein said plant of the genus Gramineae is rice.

In the present invention, the term "long-chain DNA" means a DNA of at least 30 kb, and the term "washing" means washing protoplasts with an isotonic solution or a culture medium. Furthermore, the term "gentle stirring" means stirring at a speed so as not to disrupt protoplasts.

The present invention relates to a polyethylene glycol method that enables transferring a long-chain DNA into plant cells. In the present invention, a protoplast suspension, polyethylene glycol, and a long-chain DNA are first mixed. The final concentration of protoplasts in the protoplast suspension used for mixing is usually $1 \times 10^6$ to $2 \times 10^7$ cells/ml. Protoplasts can be isolated from plant cells. For plants of the genus Gramineae, the isolation methods include, the method of Fujimura et al. [Fujimura, T., Sakurai, M., Akagi, H., Negishi, T., and Hirose, A. (1985) Regeneration of rice plants from protoplasts, Plant Tissue Culture Lett. 2: 74–75, Lorz, H., Gobel, E., and Brown, P. (1988) Advances in tissue culture and progress towards genetic transformation of cereals, Plant breeding 100: 1–25]. Furthermore, in the present invention, there are no particular limitations in the plant species to which a gene can be transferred. The final concentration of polyethylene glycol used in the mixing step is usually 10 to 30%. The final concentration of a long-chain DNA varies depending on the species of plant cells from which protoplasts are derived, but it is usually at least 50 μg/ml, preferably at least 80 μg/ml, and more preferably at least 100 μg/ml. Although in the ordinary polyethylene glycol method, the concentration of a long-chain DNA is usually 5 to 20 μg/ml, the method of the present invention is characterized by mixing a high concentration of a long-chain DNA as described above. There are no particular limitations in the type of a long-chain DNA. A circular DNA may be used as well as a linear DNA. When a vector is used to transfer a gene, any vector can be used without particular limitations.

After the above-described mixing, the gene transfer reaction is usually performed at about 20° C. for 5 to 15 min. In this reaction step, polyethylene glycol absorbs a long-chain DNA then the binding product acts on protoplasts. When a long-chain DNA is used, polyethylene glycol may form a precipitate with a long-chain DNA (hereafter termed "polyethylene glycol precipitation") to thereby cause aggregation of protoplasts in this reaction step. Such aggregation is prone to occur especially when a long-chain DNA of nearly 100 kb is used.

In the method of this invention, protoplasts are then collected, washed, and incubated in a culture medium. Protoplasts are usually recovered either by centrifugation or by allowing protoplasts to precipitate by standing, then removing the supernatant of protoplasts. The washing is usually performed using an isotonic solution such as a mannitol solution, followed by the culture medium. The washing may be repeated if necessary. However, when protoplasts aggregate due to the polyethylene glycol precipitation, it is difficult to quickly suspend them in the washing solutions. In such a case, it is preferable to dissolve the precipitated DNA by allowing it to stand or gently stirring to suspend the protoplasts in order to prevent destruction of protoplasts. The culturing conditions of the washed protoplasts vary depending on the species of plant cells from which protoplasts are derived. For example, rice protoplasts are cultured in N6 medium for about 7 to 10 days (Fujimura, T., Sakurai, M., Akagi, H., Negishi, T. and Hirose, A. (1985) Regeneration of rice plants from protoplasts, Plant Tissue Culture Lett. 2: 74–75).

In the present invention, transformed cells are then selected. This selection is usually performed using hygromycin and bialaphos (Tada, Y., Sakamoto, M. and Fujimura, T. (1990) Efficient gene introduction into rice by electroporation and analysis of transgenic plants: Use of electroporation buffer lacking chloride ions. Theor. Appl. Genet. 80: 475–480, Rao, K. V., Rathore, K. and Hodges, T. K. (1995) Physical, chemical and physiological parameters for electroporation-mediated gene delivery into rice protoplasts, Transgenic Research 4: 361–368).

The transformed cells thus selected can be redifferentiated if necessary to generate transgenic plants. Methods of redifferentiation vary depending on the species of plant cells. For example, the method of Tukahara et al. can be applied for rice, and that of Duncan et al. for corn (Tsukahara, M. and Hirisawa, T. (1992) Characterization of factors affecting plantlet regeneration from rice (*Oryza sativa* L.) callus. Bot. Mag. Tokyo 105: 227–233, Duncan, D. R., Williams, M. E., Zehr, B. E. and Widholm, J. M. (1985). The production of callus capable of plant regeneration from immature embryos of numerous *Zea mays* genotypes, Planta 165: 322–332).

DETAILED DESCRIPTION OF THE INVENTION

The following examples further illustrate the present invention but are not to be construed to limit the scope of the invention.

EXAMPLE 1
Callus Formation of the Plant Used

Mature seeds of Nihonbare rice were sterilized and sowed on N6 solid medium (containing 1 mg/l of 2,4-D, 10 mM of proline, 300 mg/l of casein hydrolysate, 30 g/l of sucrose, and 3 g/l of gellan gum). On the third week after sowing, calli were transplanted to a liquid N6 medium (containing 1 mg/l of 2,4-D, 10 mM of proline, 300 mg/l of casein hydrolysate, and 30 g/l of sucrose). After one-week liquid culture, calli were transplanted to an MS medium (containing 1 mg/l of 2,4-D and 60 g/l of sucrose). Calli on the fourth day of culturing were used to isolate protoplasts.

EXAMPLE 2
Isolation of Plasmid

Figure 1:
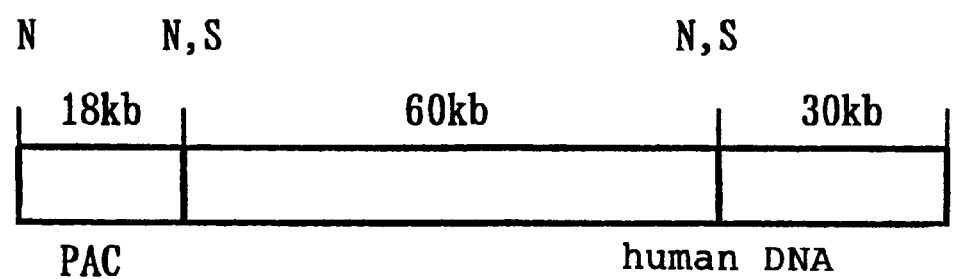
FIG. 1 shows "PAC2" used for the gene transfer into protoplasts in the present invention. In the figure, "N" and "S" stand for the Not1 site and the Sal1 site.

According to the standard method (Ausubel, F. M., Brent, R., Kingston, R. E., Moore, D. D., Seidman, J. G., Smith, J. A. and Struhl, K. ed. (1994) Current Protocols in Molecular Biology. Current Protocols: Greene Publishing Associates and Wiley-Interscience. JA), the plasmid "pucHPT" having a bacterial hygromycin-resistance gene (Tada, Y., Sakamoto, M. and Fujimura, T. (1990) Efficient gene introduction into rice by electroporation and analysis of transgenic plants: use of electroporation buffer lacking chloride ions. Theor. Appl. Genet. 80: 475–480) and "PAC" having a human gene of about 90 kb were extracted by the alkaline SDS method. (Hereafter "PAC" with the human gene is referred to as "PAC2," which is shown in FIG. 1 (K. Aschworth, M. Alegria-Hartman, M. Burgin, L. Devlin, A. V. Carrano and M. A. Batzer (1995) Assembly of high-resolution bacterial artificial chromosome, P1-derived artificial chromosome, and cosmid contigs. L. Anal. Biochem. 224: 564–571)) The extract was ultracentrifuged to be subjected to transformation.

EXAMPLE 3
Isolation of Protoplasts and Transformation by the Polyethylene Glycol Method Using the method of Tada et al. (Tada, Y., Sakamoto, M. and Fujimura, T. (1990) Efficient gene introduction into rice by electroporation and analysis of transgenic plants: use of electroporation buffer lacking chloride ions. Theor. Appl. Genet. 80: 475–480), protoplasts were isolated and suspended in 0.4 M mannitol solution containing 0.5% calcium chloride to yield a cell density of $2 \times 10^7$ cells. "pucHPT" and "PAC2" were added to this suspension to produce final concentrations of 20 μg/ml and 100 μg/ml to adjust the cell density to $1 \times 10^7$ cells. A 1-ml aliquot each of the suspensions was distributed in centrifuge tubes. To the resulting suspension was added 1 ml of a 40% polyethylene glycol solution (PEG6000) prepared according to the report by Datta et al. (Datta, S. K., Peterhans, A., Datta, K., Potrykus, I. (1990) Genetically engineered fertile indica-rice recovered from protoplasts), and the mixture was gently stirred. After the DNA formed polyethylene glycol precipitates and protoplasts aggregated with the precipitates, the mixture was allowed to stand for 10 min. After the mixture was centrifuged at 400 rpm for 3 min, the supernatant was discarded and 9 ml of a 0.4 M mannitol solution was added to the residue. The mixture was gently mixed once or twice and allowed to stand for 30 min. The same procedure was repeated and the mixture was allowed to stand for 30 min. It was centrifuged at 400 rpm, and the supernatant was discarded. 9 ml of an R2 medium (2,4-D (2 mg/l) in 0.4 M sucrose) was then added to the residue. The resulting solution was gently stirred and allowed to stand for 1 h. This procedure was repeated once more. After the disappearance of protoplast aggregation was confirmed, protoplasts were cultured according to the method of Fujimura et al. (Fujimura, T., Sakurai, M., Akagi, H., Negishi, T. and Hirose, A. (1985) Regeneration of rice plants from protoplasts. Plant Tissue Culture Lett. 2: 74–75).

On the 10th day of culturing, nurse cells (Ozawa, K. and Komamine, A. (1996) High-frequency somatic embryogenesis for small suspension-cultured clusters of cells of an interspecific hybrid of Oryza. Plant Cell, Tissue and Organ Culture 46: 157–159) were removed together with the medium, and an N6 medium (1 mg/l of 2,4-D and 0.2 M of sucrose) supplemented with hygromycin (50 mg/l) was added to select hygromycin resistance calli. After 10 days, the growing cell clusters were transferred to an N6 medium (containing 1 mg/l of 2,4-D, 10 mM of proline, 300 mg/l of casein hydrolysate, 30 g/L of sucrose, 3 g/l of gellan gum, and 50 mg/l of hygromycin). This transformation experiment was repeated three times. Hygromycin resistant calli were generated with the usual transformation efficiency.

After 10 days, growing calli were transplanted to a redifferentiation medium and allowed to regenerate plantlets according to the method of Tsukahara et al. (Tsukahara, M. and Hirisawa, T. (1992) Characterization of factors affecting plantlet regeneration from rice (*Oryza sativa* L.) callus. Bot. Mag. Tokyo 105: 227–233).

EXAMPLE 4
Identification of the Transferred Gene

A genomic DNA of the transformed plantlet was extracted, digested with the restriction enzyme EcoRI, and then subjected to electrophoresis according to the "Plant molecular biology manual." Southern hybridization was then performed using the transferred "PAC2" as a probe according to "Current protocols in molecular biology."

Figure 2:
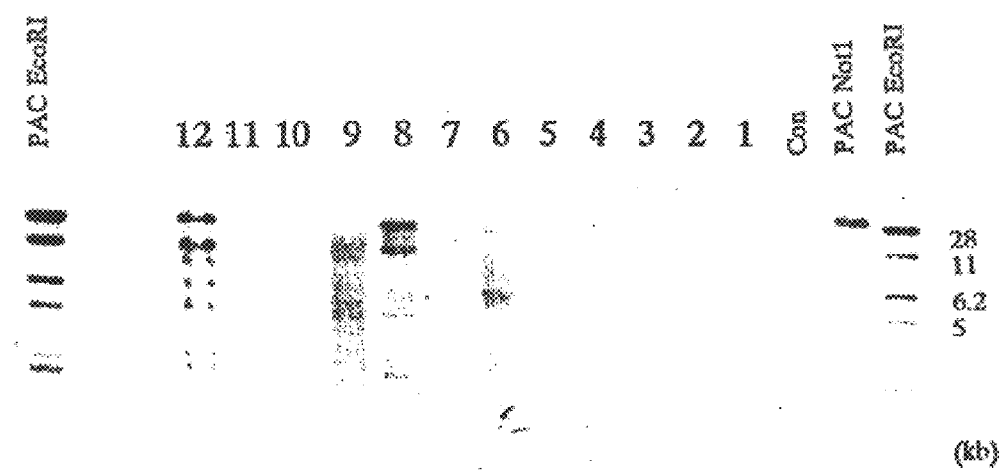
FIG. 2 shows the result of Southern hybridization of the DNA of the plant to which "PAC2" has been transferred by the polyethylene glycol method of this invention.

Twelve regenerated plantlets each were selected in three independent experiments and analyzed for the introduced gene. The human DNA bands derived from "PAC2" were detected in 8, 7 and 7 plantlets in the twelve hygromycin resistance plantlets obtained in each experiment. FIG. 2 shows the results of Southern hybridization of the experiment where eight transformed plantlets were detected. Bands were found in lanes 1, 2, 4, 6, 7, 8, 9, and 12. In FIG. 2, "PAC EcoRI" stands for bands of "PAC2" treated with EcoRI; "PAC NotI," for "PAC2" treated with NotI; and "Con," for the transformant in which only "pucHPT" was inserted. Lanes 1 to 12 shows transformants in which "pucHPT" and "PAC2" were inserted.

Figure 3:
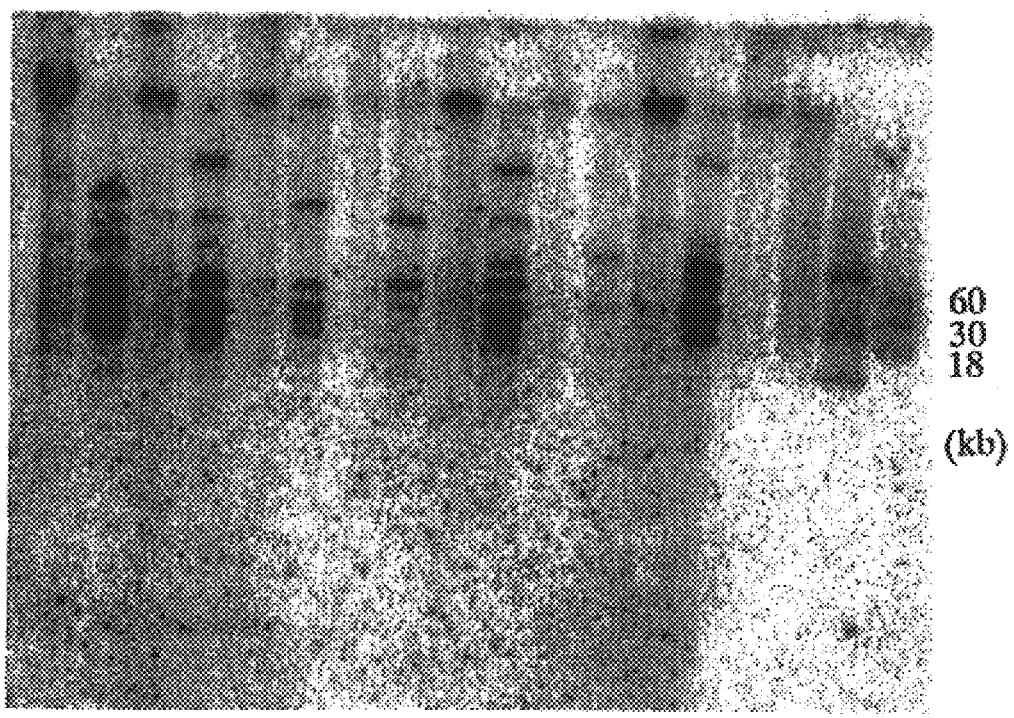
FIG. 3 shows a pulse field gel electrophoretic pattern of the DNA of the plant to which "PAC2" has been transferred by the polyethylene glycol method of this invention.

Plantlets that produced a 28 kb DNA band were subjected to pulsed field electrophoresis to detect long-chain DNA fragments. As a result, 60 kb DNA bands derived from "PAC2" were identified in two, three, and two plantlets in this pulsed field electrophoresis. FIG. 3 shows the results of pulsed field electrophoresis performed on seven transformants for which 28 kb DNA bands were detected in the above-described three Southern hybridization experiments. In FIG. 3, "N" stands for plantlets treated with Not1; "No," for plantlets not treated with the restriction enzyme; "C," for the transformant in which only "pucHPT" was inserted; and "R1" to "R12," transformants in which "pucHPT" and "PAC2" were inserted. Some transformants for which a 60 kb DNA band was identified also produced 30 kb and 18 kb bands. These results demonstrate that the whole length of "PAC2" was introduced into the plant.

Although transformants were obtained when "pAC2" was used for the gene transfer in a concentration of at least 50 µg/ml, transformants were obtained with higher gene transfer efficiency when "PAC2" concentration exceeded 50 µg/ml (for example, 80 µg/ml and 100 µg/ml).

INDUSTRIAL APPLICABILITY

The present invention provides a polyethylene glycol method that enables transferring a long-chain DNA into plant cells. According to the polyethylene glycol method of this invention, a long-chain DNA can be conveniently and highly efficiently transferred into plant cells using the purified long-chain DNA without any limitation of the plasmids used. Furthermore, the method of this invention applies to any plant species and enables the transfer of a long-chain DNA into a wide variety of plant cells.

What is claimed is:

1. A method for transferring a long-chain DNA into protoplasts, comprising the steps of:
    (a) mixing a suspension of protoplasts, polyethylene glycol, and a long-chain DNA of up to about 108 kb in length to give a final concentration of the DNA of at least 50 µg/ml;
    (b) collecting, washing, and culturing the protoplasts in a medium; and
    (c) selecting transformed cells.

2. A method for transferring a long-chain DNA into protoplasts, comprising the steps of:
    (a) mixing a suspension of protoplasts, polyethylene glycol, and a long-chain DNA of up to about 108 kb in length to give a final concentration of the DNA of at least 100 µg/ml;
    (b) collecting, washing, and culturing the protoplasts in a medium; and
    (c) selecting transformed cells.

3. The method of claim 1, wherein, in the washing of the protoplast in the step of collecting, washing, and culturing the protoplasts in a medium, a precipitated DNA is dissolved by allowing it to stand or by gently stirring to suspend the protoplasts.

4. The method of claim 1, wherein said long-chain DNA is of 100 kb or more.

5. The method of claim 1, wherein said protoplasts are derived from a monocotyledonous plant.

6. The method of claim 5, wherein said monocotyledonous plant is a plant of the family Gramineae.

7. The method of claim 6, wherein said plant of the family Gramineae is rice.

8. The method of claim 2, wherein, in the washing of the protoplast in the step of collecting, washing, and culturing the protoplasts in a medium, a precipitated DNA is dissolved by allowing it to stand or by gently stirring to suspend the protoplasts.

9. The method of claim 2, wherein said long-chain DNA is of 100 kb or more.

10. The method of claim 2, wherein said protoplasts are derived from a monocotyledonous plant.

11. The method of claim 10, wherein said monocotyledonous plant is a plant of the family Gramineae.

12. The method of claim 11, wherein said plant of the family Gramineae is rice.

* * * * *

UNITED STATES PATENT AND TRADEMARK OFFICE
CERTIFICATE OF CORRECTION

PATENT NO. : 6,143,949
DATED : November 7, 2000
INVENTOR(S) : Kenjirou Ozawa, Yasunobu Ohkawa and Teruo Ishige It is certified that error appears in the above-identified patent and that said Letters Patent is hereby corrected as shown below:

Title page,
Item [56], References Cited, OTHER PUBLICAITONS,
"Duncan et al.," reference, delete "Planta 165:322-4332" and replace with -- Planta 165:322-332 --.
"Ozawa et al.," reference, delete "Intersfecific" and replace with -- Interspecific --.

Signed and Sealed this

Twenty-second Day of March, 2005

JON W. DUDAS
*Director of the United States Patent and Trademark Office*